(12) United States Patent
Atkinson et al.

(10) Patent No.: US 10,453,665 B2
(45) Date of Patent: Oct. 22, 2019

(54) ION MODIFICATION

(71) Applicants: Jonathan Atkinson, Watford (GB); Alastair Clark, Watford (GB); Bruce Grant, Watford (GB)

(72) Inventors: Jonathan Atkinson, Watford (GB); Alastair Clark, Watford (GB); Bruce Grant, Watford (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 0 days.

(21) Appl. No.: 14/913,946

(22) PCT Filed: Aug. 19, 2014

(86) PCT No.: PCT/GB2014/052540
§ 371 (c)(1),
(2) Date: Feb. 23, 2016

(87) PCT Pub. No.: WO2015/025153
PCT Pub. Date: Feb. 26, 2015

(65) Prior Publication Data
US 2016/0203967 A1     Jul. 14, 2016

(30) Foreign Application Priority Data
Aug. 23, 2013 (GB) .................................. 1315145.1

(51) Int. Cl.
*G01N 27/62* (2006.01)
*H01J 49/06* (2006.01)
*H01J 49/00* (2006.01)

(52) U.S. Cl.
CPC .......... *H01J 49/061* (2013.01); *G01N 27/622* (2013.01); *H01J 49/0045* (2013.01)

(58) Field of Classification Search
CPC ... H01J 49/061; H01J 49/0045; G01N 27/622
See application file for complete search history.

(56) References Cited

U.S. PATENT DOCUMENTS 7,265,345 B2 *  9/2007  Hashimoto .......... G01N 27/622
                                                    250/281
7,378,650 B2 *  5/2008  Hashimoto .......... G01N 27/622
                                                    250/281

(Continued)

FOREIGN PATENT DOCUMENTS

CN      101641593 A     2/2010
CN      101688848 A     3/2010

(Continued)

OTHER PUBLICATIONS

International Search Report dated Dec. 12, 2014 for Appln. No. PCT/GB2014/052540.

(Continued)

*Primary Examiner* — Wyatt A Stoffa
(74) *Attorney, Agent, or Firm* — Kevin E. West; Advent, LLP

(57) ABSTRACT

An ion mobility spectrometer comprising an ionizer for ionizing a sample; a detector separated from the ionizer by a drift chamber along which ions can travel from the ionizer toward the detector; a gate for controlling the passage of ions from the ionizer to the drift chamber; an ion modifier arranged between the ionizer and the detector and comprising a first electrode and a second electrode; and a voltage provider configured to provide a time varying voltage between the first electrode and the second electrode wherein the time varying voltage has a frequency of at least 2.5 MHz.

18 Claims, 7 Drawing Sheets

(56) References Cited

U.S. PATENT DOCUMENTS

| | | | | |
|---|---|---|---|---|
| 7,910,878 B2* | 3/2011 | Bowdler | ............... | H01J 49/06 250/281 |
| 2003/0132379 A1* | 7/2003 | Li | ............... | G01N 27/622 250/286 |
| 2006/0071159 A1 | 4/2006 | Hashimoto et al. | | |
| 2007/0187591 A1* | 8/2007 | Bromberg | ............ | H01J 49/004 250/290 |
| 2007/0290128 A1* | 12/2007 | Hashimoto | ......... | G01N 27/622 250/286 |
| 2008/0210861 A1* | 9/2008 | Wu | ............... | G01N 27/624 250/287 |
| 2008/0230688 A1* | 9/2008 | Bowdler | ............ | H01J 49/061 250/282 |
| 2009/0039248 A1* | 2/2009 | Atkinson | ............. | G01N 27/68 250/286 |
| 2010/0051800 A1 | 3/2010 | Atkinson | | |
| 2010/0200745 A1* | 8/2010 | Osgood | ............. | G01N 27/622 250/282 |
| 2010/0314548 A1 | 12/2010 | Munchmeyer et al. | | |
| 2011/0284739 A1* | 11/2011 | Atkinson | ............. | G01N 27/68 250/283 |
| 2013/0299712 A1* | 11/2013 | Atkinson | ............. | G01N 27/622 250/389 |
| 2014/0008527 A1* | 1/2014 | Atkinson | ............. | G01N 27/68 250/282 |
| 2015/0233866 A1* | 8/2015 | Verenchikov | ....... | G01N 27/622 250/282 |
| 2017/0089863 A1* | 3/2017 | Taylor | ............... | G01N 27/622 |

FOREIGN PATENT DOCUMENTS

| | | | |
|---|---|---|---|
| CN | 101918827 | A | 12/2010 |
| CN | 102723254 | A | 10/2012 |
| CN | 103107060 | A | 5/2013 |
| EP | 1884980 | A1 | 2/2008 |
| EP | 2122340 | B1 | 11/2011 |
| GB | 2421842 | A | 7/2006 |
| GB | 2421843 | A | 7/2006 |
| GB | 2439814 | A | 1/2008 |
| GB | 2443952 | A | 5/2008 |
| GB | 2471581 | A | 1/2011 |
| GB | 2531285 | A | 4/2016 |
| GB | 2531292 | A | 4/2016 |
| JP | 2011510273 | A | 3/2011 |
| MX | 2009009402 | A | 4/2010 |
| WO | 0077823 | A2 | 12/2000 |
| WO | 0077823 | A3 | 12/2000 |
| WO | 2006114580 | A1 | 11/2006 |
| WO | 2008110754 | A2 | 9/2008 |
| WO | 2008110754 | A3 | 9/2008 |
| WO | 2012098364 | A8 | 7/2012 |
| WO | 2013093515 | A1 | 6/2013 |
| WO | 2013121287 | A1 | 8/2013 |
| WO | WO2013121287 | A1 * | 8/2013 |
| WO | 2015025153 | A1 | 2/2015 |

OTHER PUBLICATIONS

GB Search Report dated Apr. 2, 2014 for GB Application No. 1315145.1.
GB Search Report dated May 20, 2015 for GB Application No. 1414715.1.
Office Action dated Feb. 7, 2018 for Chinese Appln. No. 201480046700.2.
Examination Report dated Aug. 21, 2017 for European Appln. No. 14759047.5-1559.
Search Report dated May 3, 2016 for United Kingdom Appln. No. GB1414715.1.
Office Action from Russian Patent Appln No. 2016107757/07, dated Jun. 18, 2018.
Office Action from Mexican Patent Appln No. MX/a/2016/002317, dated Jul. 12, 2018.
Office Action from Japanese Patent Appln No. 2016-535527, dated Sep. 4, 2018.

* cited by examiner

ION MODIFICATION

The present disclosure relates to apparatus and methods, and more particularly to spectrometers, and to spectrometry methods.

Ion mobility spectrometers (IMS) can identify material from a sample of interest by ionizing the material (e.g., molecules, atoms, and so forth) and measuring the time it takes the resulting ions to travel a known distance under a known electric field. Each ion's time of flight can be measured by a detector, and the time of flight is associated with the ion's mobility. An ion's mobility relates to its mass and geometry. Therefore, by measuring the time of flight of an ion in the detector it is possible to infer an identity for the ion. These times of flight may be displayed graphically or numerically as a plasmagram. Other types of spectrometers, such as mass spectrometers, also analyse ions according to their mobility as determined by their mass-charge ratio.

To improve the ability of a spectrometer to identify ions in a sample of interest, it is suggested to modify some of the ions using a radio frequency, RF, electric field (e.g. by fragmenting them) to provide additional information which can be used to infer an identity for the ions. This provides additional degrees of freedom in the measurement of the ions, and therefore may improve the ability to resolve differences between ions. Where measurements are performed in the presence of contaminants, or in difficult operating conditions, or where a sample comprises ions with similar geometries and masses etc. the IMS's ability to detect and identify ions, and ion modification is one way to address these issues.

It is desirable to increase the proportion of ions that are modified by the application of radio frequency electric field, and the energy efficiency of the modification process.

Embodiments of the disclosure will now be described, by way of example only, with reference to the accompanying drawings, in which.

Figure 6:
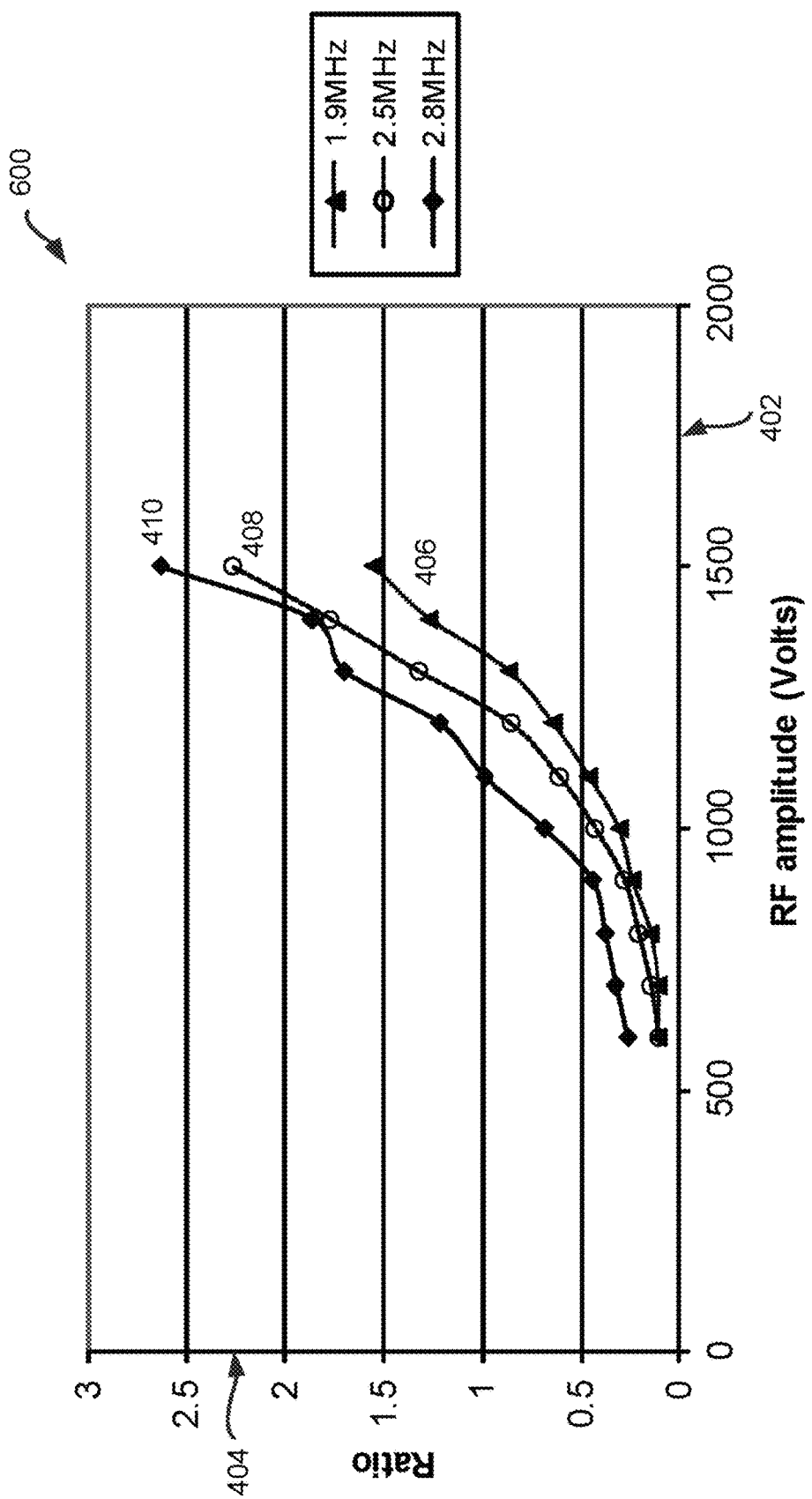
Figure 7:
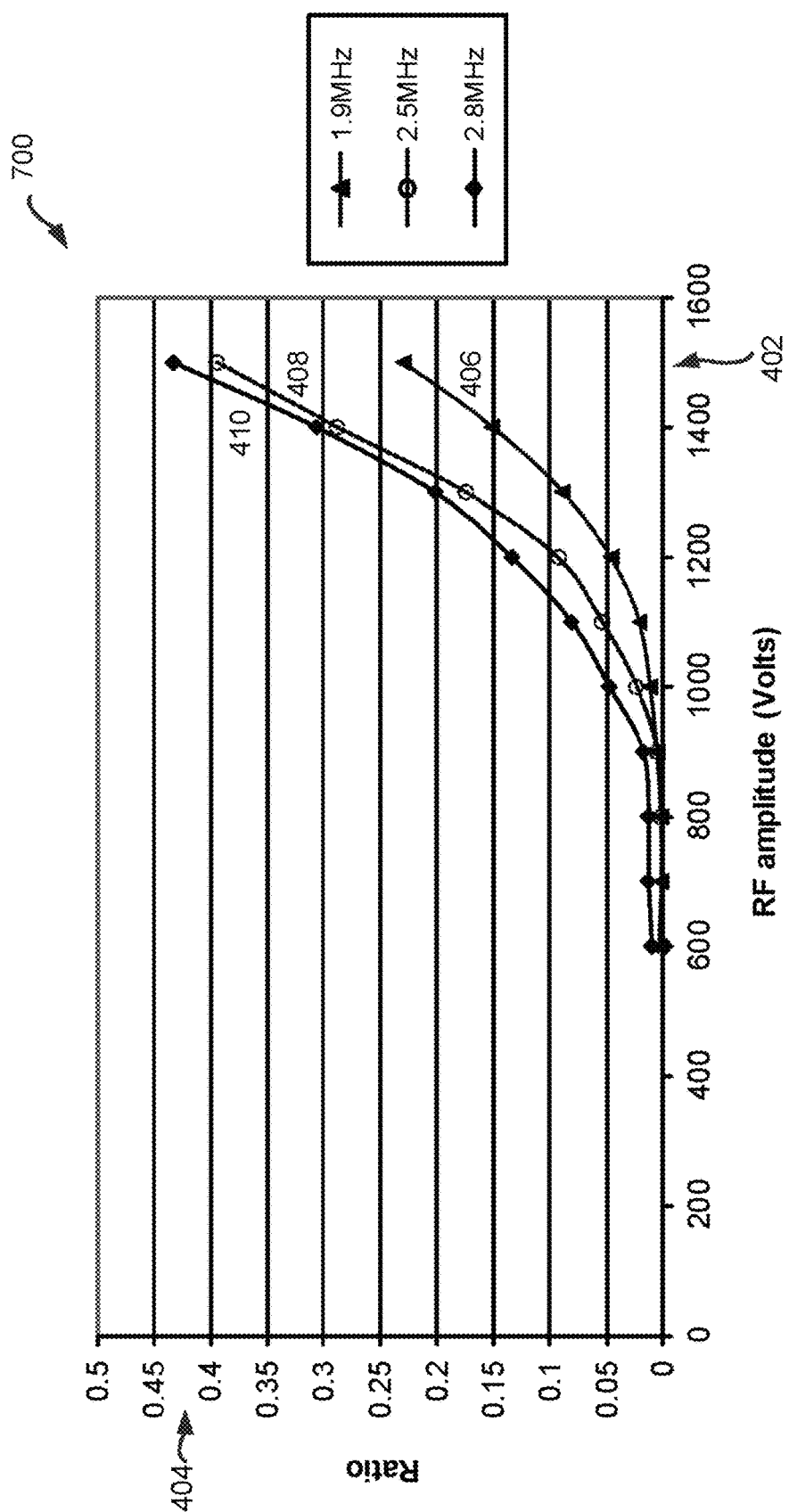

FIG. 6 shows another graph indicating the ratio of peak amplitudes between parent and daughter ions as a function of applied ion modification voltage at a selection of different frequencies of the ion modification voltage; and FIG. 7 shows yet another graph indicating the ratio of peak amplitudes between parent and daughter ions as a function of applied ion modification voltage at a selection of different frequencies of the ion modification voltage.

In the drawings like reference numerals are used to indicate like elements.

Aspects of the disclosure relate to the application of a high frequency alternating electric field to modify ions from a sample of interest. Despite the prevailing prejudice in the art, it has been found that the use of higher frequency electric fields, such as frequencies of 2.5 MHz or higher, can surprisingly increase the effectiveness of ion modification.

An ion modifier can be arranged between an ioniser and a detector in the path of ions travelling from the ioniser toward the detector. The ion modifier may comprise two electrodes, and ions travelling through the region between the two electrodes can be subjected to an alternating electric field. In aspects of the disclosure the voltage of one of the ion modifier electrodes may be controlled to vary less than the voltage of the other electrode.

In an aspect of the disclosure, a first electrode of an ion modifier may comprise conductors arranged across the direction of travel of the ions, with gaps between the conductors through which the ions can pass. A second electrode of the ion modifier may comprise conductors arranged in the path of ions travelling through the gaps in the first electrode. It may have been assumed that increasing the number of obstacles in the path of ions travelling along a detector would increase the number of ions that would be lost, however it has been found that these embodiments of the disclosure may surprisingly increase the degree of ion modification (e.g. conversion of parent ions into daughter ions).

Figure 1:
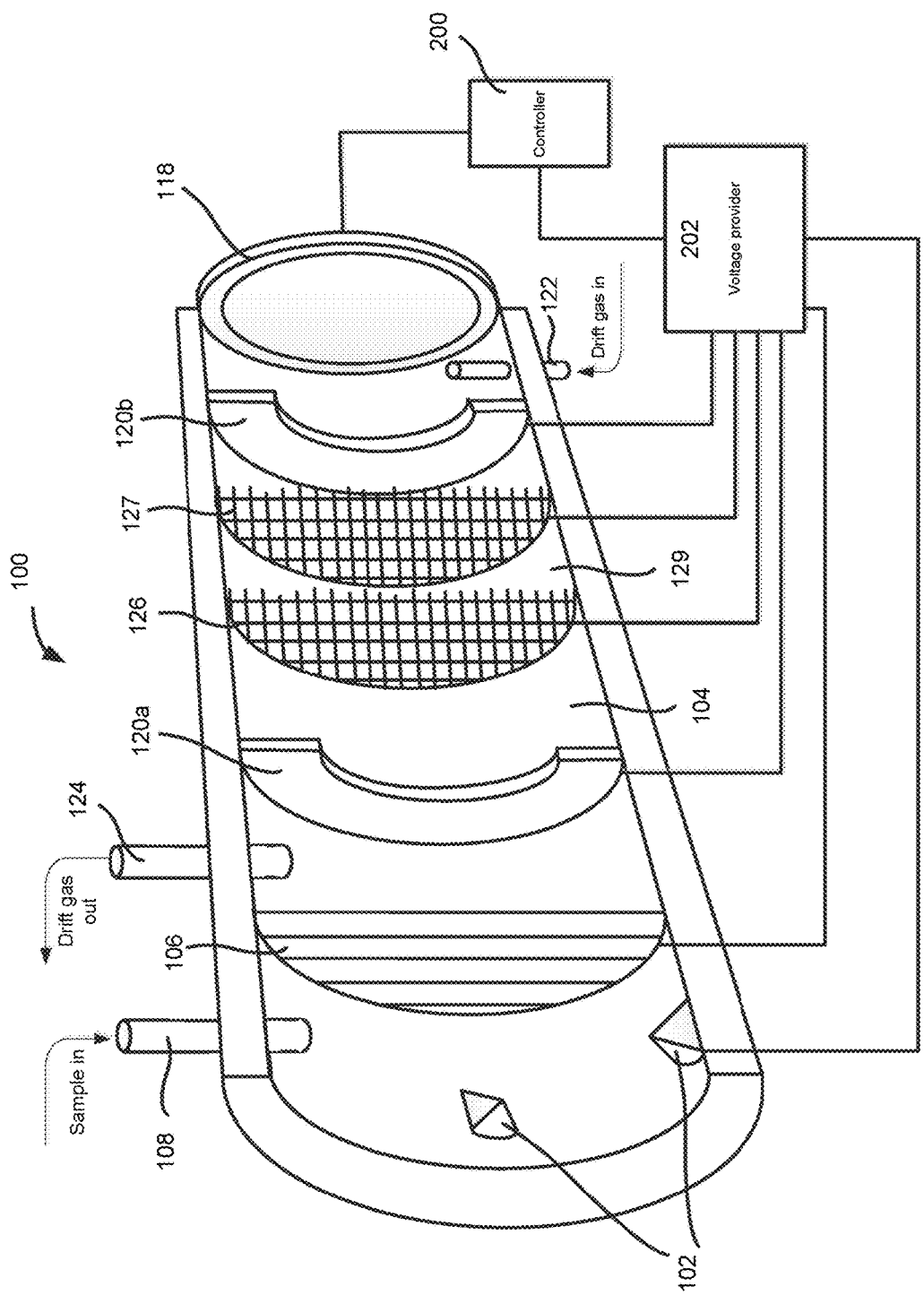
FIG. 1 is an illustration of a part section through a spectrometer.
Figure 2:
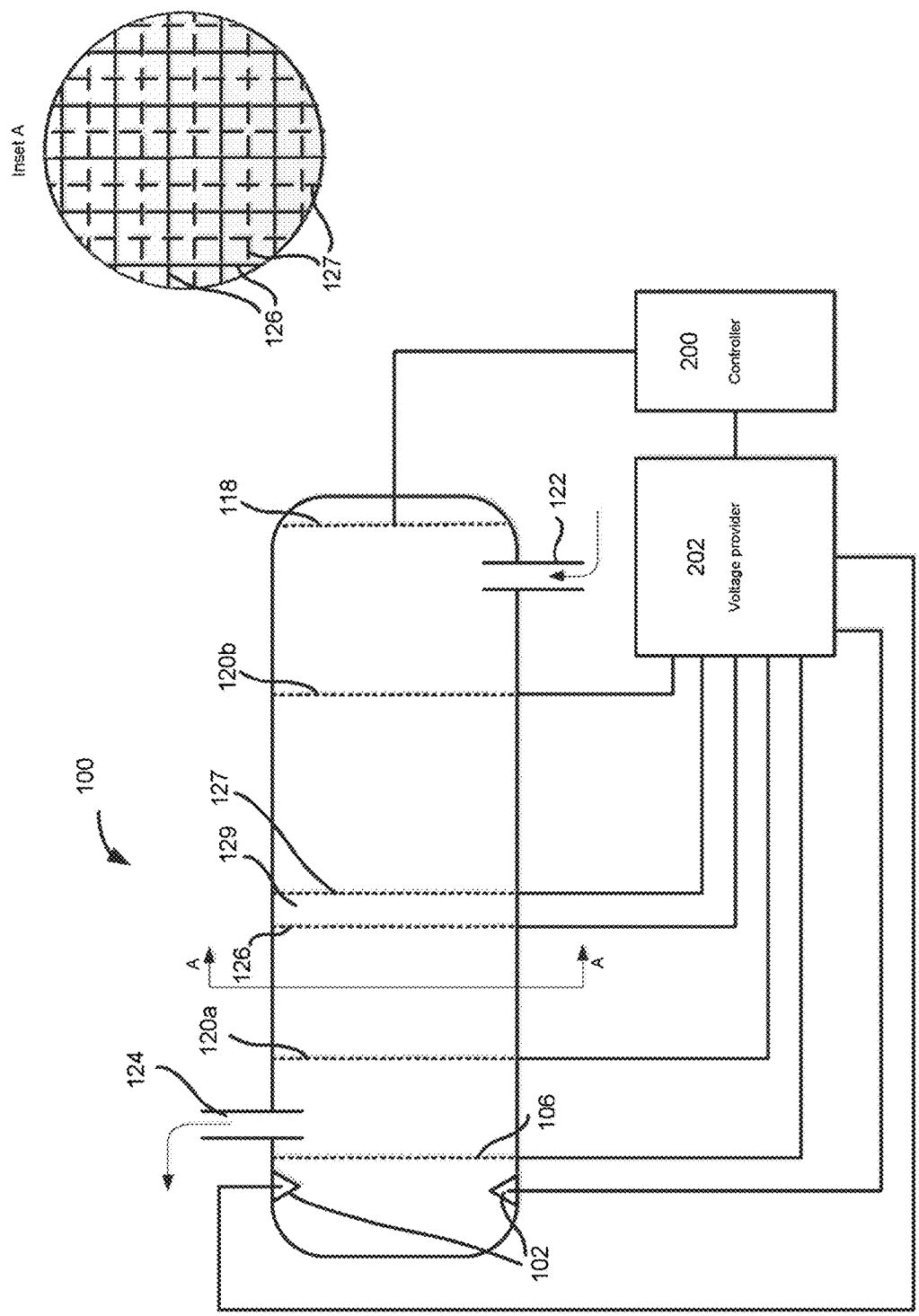
FIG. 2 shows a schematic diagram of a spectrometer illustrated in FIG. 1, and in inset shows an arrangement of ion modification electrodes.

FIG. 1 is an illustration of a part section through an ion mobility spectrometer (IMS) 100. FIG. 2 shows a schematic view of the same spectrometer. Inset A in FIG. 2 shows the arrangement of two electrodes 126, 127 viewed from the line A-A marked in FIG. 2.

The spectrometer illustrated in FIG. 1 and FIG. 2 includes an ioniser 102 that is separated from a drift chamber 104 by a gate 106. The gate 106 can control passage of ions from the ioniser 102 into the drift chamber 104. As illustrated, the IMS 100 includes an inlet 108 for enabling material to be introduced from a sample of interest to the ioniser 102.

In the example illustrated in FIG. 1, the drift chamber 104 lies between the ioniser 102 and a detector 118, so that ions can reach the detector 118 by traversing the drift chamber 104. The drift chamber 104 may comprise a series of drift electrodes 120a, 120b for applying a voltage profile along the drift chamber 104 to move ions from the ioniser 102 along the drift chamber 104 toward the detector 118.

The IMS 100 may be configured to provide a flow of drift gas in a direction generally opposite an ion's path of travel to the detector 118. For example, the drift gas can flow from adjacent the detector 118 toward the gate 106. As illustrated, a drift gas inlet 122 and drift gas outlet 124 can be used to pass drift gas through the drift chamber. Example drift gases include, but are not limited to, nitrogen, helium, air, air that is re-circulated (e.g., air that is cleaned and/or dried) and so forth.

The detector 118 may be coupled to provide a signal to a controller 200. Current flow from the detector 118 can be used by the controller 200 to infer that ions have reached the detector 118, and a characteristic of the ions can be determined based on the time for ions to pass from the gate 106 along the drift chamber 104 to the detector 118. Examples of a detector 118 are configured to provide a signal indicating that ions have arrived at the detector 118. For example, the detector may comprise a conductive electrode (such as a faraday plate), which may be charged to catch ions.

Electrodes 120a, 120b, may be arranged to guide ions toward the detector 118, for example the drift electrodes 120a, 120b may comprise rings which may be arranged around the drift chamber 104 to focus ions onto the detector 118. Although the example of FIG. 1 includes only two drift electrodes 120a, 120b, in some examples a plurality of electrodes may be used, or a single electrode may be used in combination with the detector 118 to apply an electric field to guide ions toward the detector 118.

The ion modifier electrodes 126, 127 can be spaced apart from the gate electrode 106. As illustrated, the ion modifier electrodes 126, 127 are arranged in the drift chamber, between the gate electrode and the detector. In an embodiment the ion modifier electrode may be arranged in the ionisation chamber, for example between the inlet 108 and the gate 106.

Each of the ion modifier electrodes 126, 127 can comprise an array of conductors arranged across the drift chamber. As illustrated, the conductors of each ion modifier electrode 126, 127 may have gaps between them such that ions can pass through each electrode by travelling through the gaps. In one example ions pass through the gaps between the conductors of the electrode 126, into a region 129 between the electrodes 126, 127, and out of the region through the gaps between the conductors of the electrode 127. While the ions are in the region between the electrodes 126, 127 they can be subjected to an alternating, RF, electric field.

As shown in FIG. 1 a voltage provider 202 is coupled to be controlled by the controller 200. The voltage provider 202 may also be coupled to provide voltages to the ioniser 102 to enable material from a sample to be ionised. In an embodiment the voltage provider 202 is coupled to the gate electrode 106 to control the passage of ions from the ionisation chamber into the drift chamber 104. The voltage provider 200 can be coupled to the drift electrodes 120a, 120b for providing a voltage profile for moving ions from the ioniser 102 toward the detector 118. As illustrated in FIG. 1, the voltage provider 202 is coupled to provide an alternating RF voltage to the ion modifier electrodes 126, 127. By controlling the voltage of one of the two ion modifier electrodes 126, 127 with respect to the other, the voltage provider can provide a time varying voltage between the first electrode and the second electrode. The time varying voltage has a frequency of at least 2.5 MHz. In an embodiment the frequency is at least 3 MHz, or at least 5 MHz, in some embodiments at least 6 MHz. In an embodiment the frequency is less than 100 MHz, in some embodiments the frequency is less than 50 MHz, in some embodiments less than 20 MHz, in some embodiments less than 15 MHz, or less than 10 MHz. For example, the frequency may be between 3 MHz and 20 MHz, or between 6 MHz and 12 MHz. In some examples the frequency is about 8 MHz.

In an embodiment the voltage provider is configured to control the voltage of the first electrode to vary less than the voltage of the second electrode. In an example, the amplitude of the variation of the voltage of one of the ion modifier electrodes 126, 127 may be less than the amplitude of the variation of the other ion modifier electrode. For example, the voltage provider 202 may control the voltage of one of the ion modifier electrodes based on a direct current, DC, reference voltage so that the voltage of one electrode is constant whilst the other varies. In one example the voltage provider may control the voltage of the ion modifier electrodes 126, 127 so the variation of each is sinusoidal, or a square wave, a saw tooth, or a train of pulses, and the amplitude of the variation in voltage at one ion modifier electrode may be less than the variation in voltage at the other ion modifier electrode. In embodiments, applying asymmetric voltages to the ion modifier electrodes may reduce unwanted coupling of RF electric fields with other components of the spectrometer, and this may reduce unwanted leakage of electromagnetic interference from the spectrometer.

The voltage provider 202 may control the voltage of the two ion modifier electrodes to vary with a selected phase difference, for example the voltage controller may control the voltage of the two ion modifier electrodes 126, 127 so that the positive voltage excursion of one electrode occurs during the negative voltage excursion of the other. For example, the voltage provider 202 may control the voltage of the two ion modifier electrodes 126, 127 to vary in anti-phase. The voltage excursions of the two electrodes may be of the same amplitude.

In some examples the voltage provider may control the voltage of one of the ion modifier electrodes 126, 127 to vary more quickly than the voltage of the other ion modifier electrode 126, 127. For example, one of the ion modifier electrodes 126, 127 maybe coupled to a reference voltage, which may comprise a DC voltage, whilst the other ion modifier electrode may be coupled to an alternating voltage, such as an RF voltage.

As noted above, the drift electrodes 120a, 120b may provide a voltage profile that moves ions along the drift chamber so that the ions travel from the ioniser toward the detector. As illustrated in FIG. 1, and FIG. 2, the first ion modifier electrode 126 and the second ion modifier electrode 127 can be spaced apart in the direction of travel of the ions. In an embodiment, the voltage provider is configured to control the voltage of at least one of the ion modifier electrodes 126, 127 based on the location of the ion modifier electrodes 126, 127 along the drift chamber 104 and based on the voltage profile provided by the drift electrodes 120a, 120b. In an embodiment the time average of the voltage of the ion modifier electrodes is selected based on this voltage profile. In an embodiment the voltage provider 202 provides a DC voltage offset between the ion modifier electrodes. This DC voltage offset may be based on the spacing between the ion modifier electrodes 126, 127 and the voltage profile.

As shown in FIG. 1 and FIG. 2, the ion modifier electrodes 126, 127 each comprise a grid of conductors. As illustrated in FIG. 2, the ion modifier electrodes 126, 127 may be parallel to each other. In an embodiment the grids are arranged across (e.g. transverse, or perpendicular to) the direction of travel of ions from the ioniser towards the detector.

Ions travelling towards the detector can pass through gaps between the conductors of one of the ion modifier electrodes 126, and into the region 129 between the ion modifier electrodes 126, 127 where they can be subjected to a radio frequency, RF, electric field.

The ion modifier electrode 127 that is closer to the detector 118 may be arranged so that the conductors of that electrode 127 lie in the path of ions travelling through the gaps in the other ion modifier electrode. As shown in detail in Inset A of FIG. 2, the conductors 127 of one electrode may at least partially obstruct the gaps in the other electrode 126. It has been found that this may increase the number of parent ions that are converted into daughter ions by the ion modifier. The conductors of the electrode 126 are shown as being parallel to the conductors of the electrode 127. In an embodiment, the electrodes 126, 127 may be arranged in parallel planes, but the conductors of the two electrodes 126, 127 may be angularly offset from one another (e.g. misaligned), so that the conductors of one ion modifier electrode lie in the path of ions travelling through the gaps in the other ion modifier electrode. In an embodiment, the electrodes 126, 127 may be arranged in parallel planes, but the conductors of the two electrodes 126, 127 may be laterally offset from one another, in a direction transverse to the direction of travel of the ions, so that the conductors of one ion modifier electrode 126 lie in the path of ions travelling through the gaps in the other ion modifier electrode 127. In some embodiments these features are combined so that the conductors of the two ion modifier electrodes 126, 127 are both laterally and angularly offset.

In an embodiment the spectrometer and the voltage provider may be contained in a common housing.

In an embodiment the ion modifier electrodes 126, 127 may be disposed in the drift chamber. The ion modifier electrode may be spaced along the drift chamber from the gate electrode. The spacing may be at least 0.5 mm from the gate electrode 106, for example at least 2 mm, in an embodiment at least 4 mm, in an embodiment at least 6 mm, or at least 7 mm. In an embodiment the spacing may be less than 150 mm, or less than 100 mm, for example less than 50 mm.

The electrodes 126, 127 may comprise wire mesh. The mesh may be a lattice of conductors which may be arranged in a repeating square pattern. The conductors may have a thickness of at least 10 μm, for example less than 30 μm. The pitch of the mesh may be at least 200 μm, for example less than 500 μm. The two meshes may be separated from one another by at least 0.1 mm, for example at least 0.15 mm, for example less than 0.4 mm, for example less than 0.3 mm.

In one embodiment the nearest electrode 126 is arranged in the drift region 7 mm from the gate 106. In this embodiment the spacing between the ion modifier electrodes is 0.2 mm, and the electrodes comprise a mesh having a square pattern. In this embodiment the conductors of the mesh have a thickness of 21 μm and are arranged on a 363 μm pitch. The conductors may comprise wire.

Figure 3:
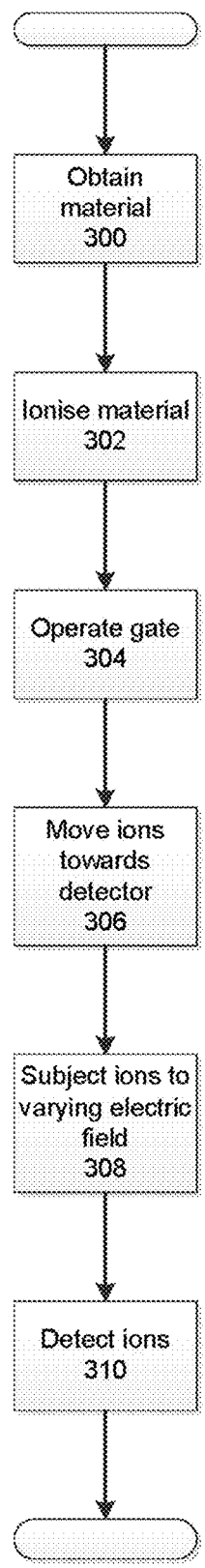
FIG. 3 shows a flow chart illustrating a method of operation of an apparatus such as that shown in FIG. 1 and FIG. 2.

A first example of operation of the apparatus shown in FIG. 1 and FIG. 2 is illustrated in FIG. 3.

As illustrated in FIG. 3, a method of modifying ions comprises obtaining 300 material from a sample of interest into an ionisation chamber of a spectrometer, and ionising 302 the material. A gate electrode can then be operated 304 to allow ions to be moved 306 from the ionisation chamber towards a detector. On the path towards the detector the ions can be moved through an ion modification region. In an embodiment the method illustrated in FIG. 3 comprises subjecting 308 that region to a time varying electric field that varies with a frequency of at least 2.5 MHz. The ions can then be detected 310 and analysed based on their times of flight from the gate to the detector.

In an embodiment the method comprises controlling a voltage at one side of the region to vary less than the voltage at the side of the region. For example the voltage at one side of the region may be controlled to vary more quickly than the voltage at the respective other side of the region.

In spectrometry ion counts may be measured by peaks on a plasmagram, and the height of a peak may be an indicator of the number of ions reaching the detector at a particular time. Ions which are produced by ion modification may be termed "daughter ions", and ions from which daughter ions are produced may be termed "parent ions"

Figure 4:
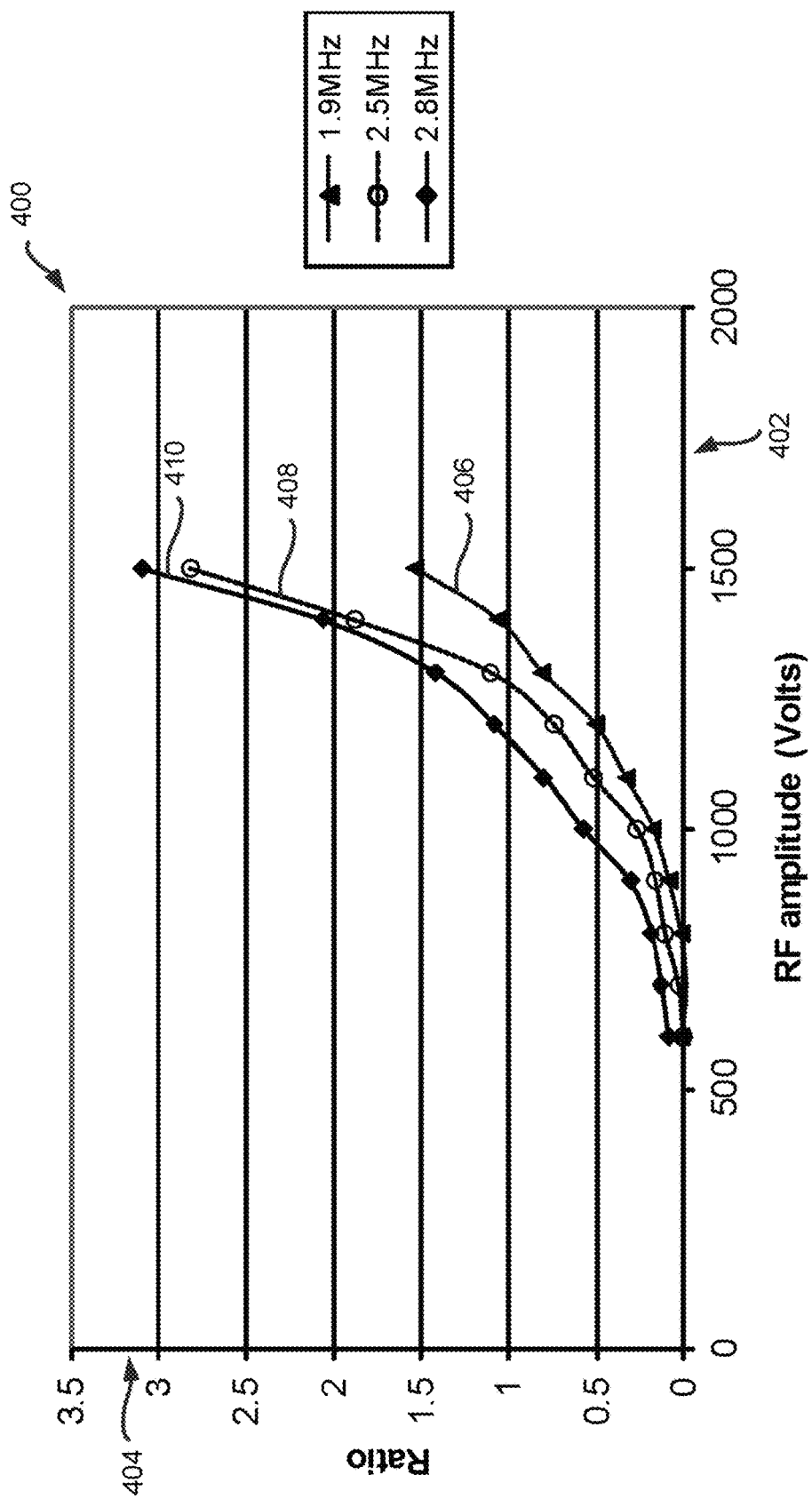
FIG. 4 shows a graph indicating the ratio of peak amplitudes between parent and daughter ions as a function of applied ion modification voltage at a selection of different frequencies of the ion modification voltage.

FIG. 4 shows a graph 400 showing three plots of the ratio of peak height associated with modified, daughter, ions to the peak height associated with parent ions of cyclohexanol.

In the graph 400 shown in FIG. 4 the x-axis, 402, indicates the applied radio frequency voltage amplitude applied to ion modifier electrodes such as the electrodes 126, 127 illustrated in FIG. 1 and FIG. 2.

The y-axis, 404, indicates the ratio of the number of daughter ions to the number of parent ions.

A first curve 406 plotted on the graph shows the ratio as a function of RF voltage amplitude where the frequency of the RF voltage is 1.9 MHz. A second curve 408 plotted on the graph shows the ratio as a function of RF voltage amplitude where the frequency of the RF voltage is 2.5 MHz. A third curve 410 plotted on the graph shows the ratio as a function of RF voltage amplitude where the frequency of the RF voltage is 2.8 MHz It can be seen in FIG. 4 that at a given RF voltage amplitude, the number of daughter ions produced is consistently greater where the RF frequency is higher, and increasing the frequency to 2.5 MHz has a very marked effect, and increasing to 2.8 MHz even more so. In some embodiments this use of higher frequency RF more than doubles the ratio at a given voltage as compared with a frequency of 1.9 MHz. As will be appreciated in the context of the present disclosure, this may provide significant efficiency gain by reducing the voltage required to achieve a given sensitivity.

It can be seen from FIG. 4 that at an RF voltage amplitude of 1500V, the daughter ion peak height was 1.5 times the height of the parent ion peak when the frequency was 1.9 MHz, whereas when the frequency was increased to 2.8 MHz the fragment peak height was over three times that of the parent ion peak height at 1500V.

Without wishing to be bound by theory it is believed that, at a frequency of 1.9 MHz, the distance that an ion travels in one half of the RF waveform is comparable to the distance between the two modifier electrodes 126, 127. As such, the ions do not experience as many cycles of the RF as they do when the frequency is increased. Put another way, if an ion has a velocity of 1000 meters per second then in one half of a 2 MHz cycle it will travel 0.25 mm if the applied voltage is a square wave, or 0.176 mm if the applied voltage is a sine wave. If the gap between the ion modifier electrodes is 0.25 mm or perhaps less it can be seen that, after only a few cycles the ion will be ejected from the ion modifier. When the frequency is increased, for example to 6 MHz, or to 8 MHz, the distance traveled in one half of a cycle reduces (e.g. becomes 0.044 mm at 8 MHz). Therefore the the ion can experience many cycles before it leaves the modifier, and the probability of it experiencing a collision with high enough energy for a bond to break or some other molecular transformation to take place can be increased.

In some embodiments even higher frequencies, for example between 8 MHz and 10 MHz may reduce ion losses in the ion modifier—again without wishing to be bound by theory, this may be because the ions are able to get closer to the conductors of the ion modifier electrodes before they reach a "point of no return" (where they will be drawn onto the conductors). As such fewer ions may hit the wires and more therefore survive the journey through the modifier further increasing sensitivity.

Figure 5:
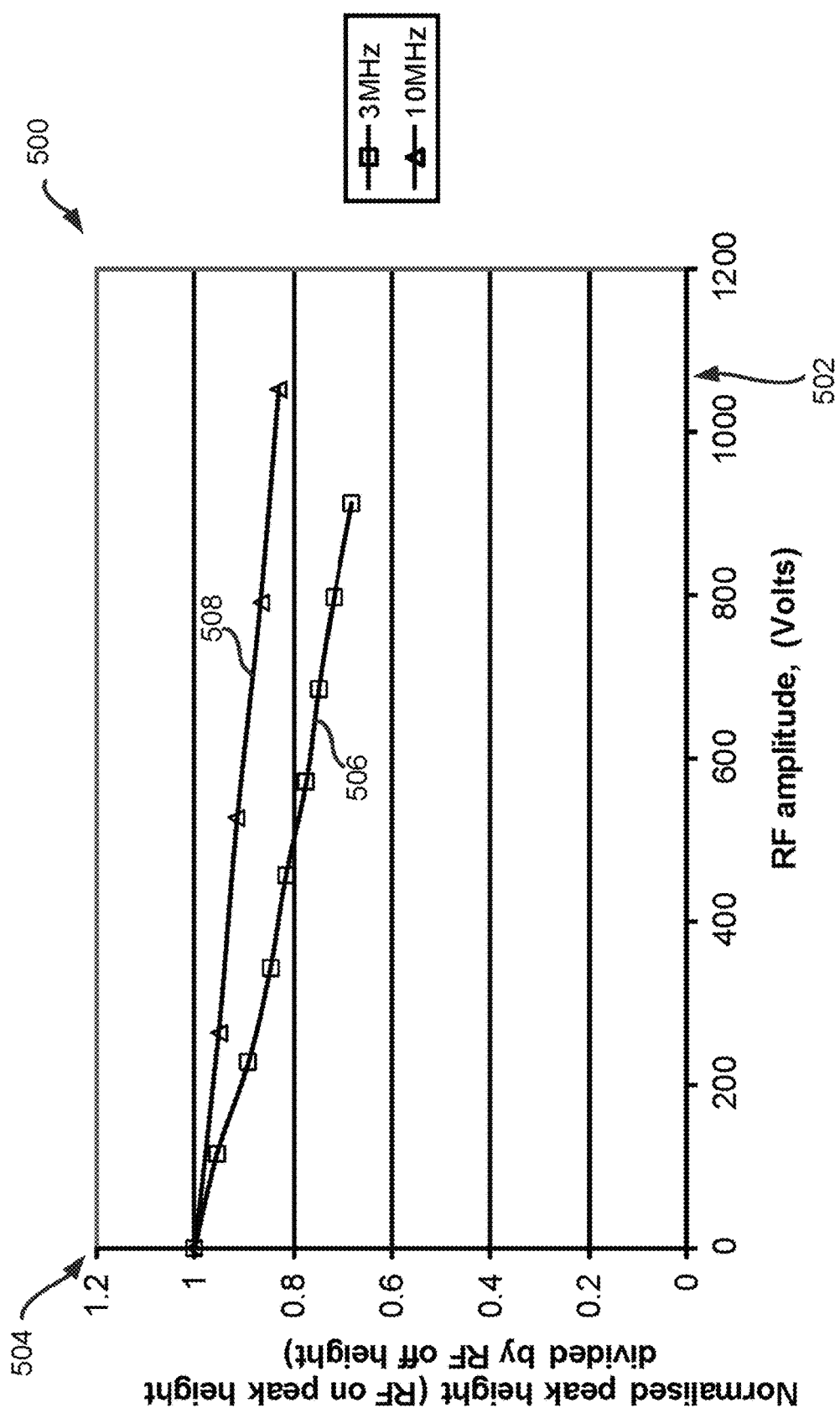
FIG. 5 shows a graph indicating ion loss as a function of applied ion modification voltage at a selection of different frequencies of the ion modification voltage.

FIG. 5 shows a graph 500 illustrating this increase in sensitivity.

In the graph 500 shown in FIG. 5 the x-axis, 502, indicates the applied radio frequency voltage amplitude applied to ion modifier electrodes such as the electrodes 126, 127 illustrated in FIG. 1 and FIG. 2. The parent ions in this example comprised the negative mode reactant ions.

The y-axis, 504, indicates the ratio of the normalised peak height comparing the peak height when the ion modifier electrodes are not operated (turned off) to the peak height when the ion modifier electrodes are operated at the voltage indicated on the x-axis 502.

A first curve 506 plotted on the graph shows the ratio as a function of RF voltage amplitude where the frequency of the RF voltage is 3 MHz. A second curve 508 plotted on the graph shows the ratio as a function of RF voltage amplitude where the frequency of the RF voltage is 10 MHz. It can be seen that there is a significant reduction in ion loss where a higher frequency is used, and this is particularly true at higher voltage amplitudes.

As in FIG. 4, FIG. 6 and FIG. 7 each show a graph 600, 700 showing three plots of the ratio of peak height associated with modified, daughter, ions to the peak height associated with parent ions. In FIG. 4, FIG. 6, and FIG. 7, like reference numerals are used to indicate like elements.

In the example 600 shown in FIG. 6 the parent ions comprise diisopropylmethylphosphonate (DIMP).

In the example 700 shown in FIG. 7, the parent ions comprise acetone.

It will be appreciated that in the context of the present disclosure that RF electric fields comprise any alternating electric field having frequency characteristics appropriate for applying energy to modify ions (e.g. by imparting energy to them to raise their effective temperature).

Other examples and variations will be apparent to the skilled reader in the context of the present disclosure.

Aspects of the disclosure provide computer program products, and computer readable media, such as tangible non-transitory media, storing instructions to program a processor to perform any one or more of the methods described herein. Other variations and modifications of the apparatus will be apparent to persons of skill in the art in the context of the present disclosure.

The invention claimed is:

1. An ion mobility spectrometer comprising:
   an ioniser for ionising a sample;
   a detector separated from the ioniser by a drift chamber along which ions can travel from the ioniser toward the detector;
   a gate for controlling the passage of ions from the ioniser to the drift chamber;
   an ion modifier arranged between the ioniser and the detector, the ion modifier including a first mesh electrode and a second mesh electrode, the ion modifier spaced apart from the gate, and the first mesh electrode and the second mesh electrode separated from one another in a direction of travel of the ions; and
   a voltage provider configured to provide a time varying voltage between the first mesh electrode and the second mesh electrode wherein the time varying voltage has a frequency of at least 2.5 MHz, and wherein the voltage provider is capable of varying the voltage of the first mesh electrode less than the voltage of the second mesh electrode.

2. The ion mobility spectrometer of claim 1 wherein the ioniser is arranged in an ionisation chamber that is separated from the drift chamber by the gate.

3. The ion mobility spectrometer of claim 1 wherein the ion modifier is arranged in one of the drift chamber and the ionisation chamber.

4. The ion mobility spectrometer of claim 3 comprising a drift gas inlet and a drift gas outlet arranged to provide a flow of drift gas along the drift chamber and through the ion modifier.

5. The ion mobility spectrometer of claim 1 wherein the voltage provider is configured to vary the voltage of the second mesh electrode more quickly than the voltage of the first mesh electrode.

6. The ion mobility spectrometer of claim 1 wherein the time varying voltage comprises time varying voltages of equal amplitude provided to the first mesh electrode and the second mesh electrode, wherein the voltage provided to the second mesh electrode is of opposite phase to the voltage provided to the first mesh electrode.

7. The ion mobility spectrometer of claim 1 wherein the voltage provider is configured to hold the voltage of the first mesh electrode at a voltage selected according to a voltage profile that moves the ions from the ioniser towards the detector and the location of the first mesh electrode along the voltage profile.

8. The ion mobility spectrometer of claim 1 wherein at least one of the first mesh electrode or the second mesh electrode comprises conductors arranged across the direction of travel of the ions, with gaps between the conductors through which the ions can travel, and the respective other one of the first mesh electrode and the second mesh electrode comprises conductors arranged across the direction of travel in the path of ions travelling through said gaps.

9. A method of modifying ions in an ion mobility spectrometer, the method comprising:
   operating a gate electrode to allow ions to be moved towards a detector;
   subjecting at least one region spaced apart from the gate electrode in the spectrometer to a time varying electric field, wherein the ions pass through the region toward the detector from a first side of the region to a second side of the region; and
   controlling a voltage of a first plurality of conductors arranged across a direction of travel of the ions, with gaps between the conductors through which the ions can pass, at one of the first side of the at least one region or the second side of the at least one region to vary less than the voltage of a second plurality of conductors arranged across a direction of travel of the ions, with gaps between the conductors through which the ions can pass, at the respective other one of the first side and the second side.

10. The method of claim 9 further comprising controlling a voltage at one of the first side of the region and the second side of the region to vary more quickly than the voltage at the respective other one of the first side of the region and the second side of the region.

11. The method of claim 9 wherein the time varying electric field comprises a component that varies with a frequency of at least 2.5 MHz.

12. A spectrometer comprising:
   an ioniser for ionising a sample;
   a detector separated from the ioniser by a drift chamber along which ions can travel from the ioniser toward the detector;
   a gate for controlling the passage of ions from the ioniser to the drift chamber; and
   an ion modifier arranged between the ioniser and the detector, the ion modifier including a first electrode and a second electrode wherein the first electrode and the second electrode are spaced apart in the direction of travel of the ions, the first electrode and the second electrode comprising conductors arranged across a direction of travel of the ions, with gaps between the conductors through which the ions can pass, wherein the conductors of the first electrode are at least one of laterally offset from the conductors of the second electrode or angularly offset from the conductors of the second electrode.

13. The spectrometer of claim 12, further comprising a voltage provider configured to provide a time varying voltage between the first electrode and the second electrode and to vary the voltage of the first electrode less than the voltage of the second electrode.

14. The spectrometer of claim 13 wherein the time varying voltage comprises a frequency component of at least 2.5 MHz.

15. The spectrometer of claim 12 wherein at least one of the first electrode or the second electrode comprises a mesh.

16. The spectrometer of claim 12, wherein the ion modifier is spaced apart from the gate.

17. The spectrometer of claim 16, wherein the ioniser is arranged in an ionisation chamber that is separated from the drift chamber by the gate.

18. The spectrometer of claim 17, wherein the ion modifier is arranged in one of the drift chamber and the ionisation chamber.

* * * * *